United States Patent [19]

Heath et al.

[11] Patent Number: 4,755,388

[45] Date of Patent: Jul. 5, 1988

[54] LIPOSOME-ENCAPSULATED 5-FLUOROPYRIMIDINES AND METHODS FOR THEIR USE

[75] Inventors: Timothy D. Heath, Madison, Wis.; Walter H. Stern, San Mateo; Demetrios Papahadjopoulos, San Francisco, both of Calif.

[73] Assignee: The Regents of the University of California, Berkeley, Calif.

[21] Appl. No.: 869,108

[22] Filed: May 30, 1986

Related U.S. Application Data

[63] Continuation-in-part of Ser. No. 670,656, Nov. 9, 1984, which is a continuation of Ser. No. 370,421, Apr. 21, 1982, abandoned.

[51] Int. Cl.$^4$ ............................................... A61K 9/42
[52] U.S. Cl. .................................... 424/450; 424/498; 264/4; 514/269; 514/274
[58] Field of Search ................ 514/269, 274; 424/498, 424/450; 264/4

[56] References Cited

U.S. PATENT DOCUMENTS 4,515,736  5/1985  Deamer ................................ 264/4.3
4,564,599  1/1986  Janoff et al. ..................... 424/498 X

FOREIGN PATENT DOCUMENTS 2041871  9/1980  United Kingdom ................ 514/274

OTHER PUBLICATIONS

Heath et al., FEBS Letters, 187(1): 73-75, Jul. 1985.

Primary Examiner—Christine M. Nucker
Attorney, Agent, or Firm—Leydig, Voit & Mayer

[57] ABSTRACT

Drugs encapsulated in liposomes are provided, where the drugs are low molecular weight, negatively charged polar drugs and the liposomes are comprised of high transition temperature phospholipids and cholesterol. Relatively large liposomes are employed to enhance drug effectiveness with viable cells.

17 Claims, No Drawings

LIPOSOME-ENCAPSULATED 5-FLUOROPYRIMIDINES AND METHODS FOR THEIR USE

This invention was made with Government support under Grant Nos. EY03228, GM31070, CA25526, and CA35340 from the National Institutes of Health and the University of California. The Government has certain rights in this invention.

The present application is a continuation-in-part of application Ser. No. 670,656, filed on Nov. 9, 1984, which is a continuation of application Ser. No. 370,421, filed on Apr. 21, 1982, now abandoned, whose disclosure is incorporated herein by reference.

BACKGROUND OF THE INVENTION

1. Field of the Invention

The use of liposomes as carriers for introducing drugs and macromolecules into cells has been reported. Liposomes are vesicles comprising a phospholipid bilayer enclosing an aqueous or partially aqueous volume produced by hydration and mechanical dispersion of lipid material in an aqueous medium. Drugs may be introduced into the aqueous volume by suspension or dissolution in the aqueous medium. It is believed that liposome-encapsulated drugs are transported essentially intact to targeted tissues and organs in the body, where they are transferred into individual cells and released. Advantages of liposome encapsulation lies in the protection of the drug while it is delivered to the organ or tissue, the liposome-mediated transport of the drug into the cell at an elevated localized concentration, and protection of the untargeted cells from the drug.

Scar tissue results from the formation of a hard layer of connective tissue formed over a healing wound or cut. In many cases, scar tissue results in tissue contraction which may result in disfiguration and, more seriously, which may produce side effects which comprise tissue and organ function. Scar tissue formation in the eye, referred to as proliferative vitreoretinopathy, frequently results in retinal detachment. Current methods for preventing such scar tissue formation in the eye, such as corticosteroids, are not always effective. Other examples of scar tissue formation which are detrimental include posterior tear capsule opacification after cataract surgery, scar tissue over filtration sites for glaucoma, scar tissue formation after skin grafting, and scar tissue formation around breast implants. All of these might benefit from fluoroorotate therapy.

It would be desirable to provide improved methods and compositions for inhibiting the formation of scar tissue under a variety of circumstances and particularly the formation of scar tissue in the eye. It is of substantial importance to be able to inhibit scar tissue without adversely affecting cells and cell processes.

2. Description of the Relevant Literature

5-Fluoroorotate is a derivative of 5-fluorouracil for which no cellular transport system exists. Bosch et al. (1958) Cancer Res. 18:335-343. Both 5-fluorouracil and 5-fluoroorotate interfere with ribosomal maturation (Wilkinson et al. (1971) J. Biol. Chem. 246:63-68 and J. Biol. Chem. 246:6418-6427) and may also be metabolized to fluorodeoxyuridine monophosphate, an inhibitor of thymidylate synthetase (Hartman and Heidelberger (1961) J. Biol. Chem. 236:3006-3013). Attempts to encapsulate 5-fluorouracil in liposomes have met with limited success. Gregoriadis et al. (1974) Lancet 1:1313-1316 and Gregoriadis (1974) Biochem. Soc. Trans. 2:117. Heath et al., ARAVO Abstracts, p. 284, 8-10:15, May 10, 1985, report advantages of encapsulating 5-fluoroorotate for treatment of retinal detachment.

SUMMARY OF THE INVENTION

According the the present invention, physiologically active agents are provided comprising negatively charged low molecular weight polar drugs in the lumen of liposomes of predetermined composition and size range. Paradigmatically, 5-fluoroorotate is encapsulated in relatively large liposomes employing combinations of diacylphosphatidylglycerol and cholesterol, particularly with acyl groups of from 16 to 18 carbon atoms. The subject drug inhibits cell contraction and cell growth. Use of specific compounds associated with the subject agents can be used for site-directed treatment of diseased or other aberrant physiological state.

DESCRIPTION OF THE SPECIFIC EMBODIMENTS

Novel compositions are provided for enchancing physiological activity of low molecular weight drugs, particularly polar drugs having negative charges and molecular weights of from about 150 to 350 Daltons. The drugs are administered in the lumen of relatively large non-leaky vesicles composed of high-phase-transition-temperature phospholipids and steroids, particularly cholesterol. The vesicle reagents are prepared by conventional techniques, preferably providing relatively large diameter liposomes. Particular combinations of drugs and lipids provide for stable vesicles, which may be employed in vitro and in vivo for enhanced drug activity.

The drugs which find use are relatively low molecular weight polar drugs having a negative charge, particularly carboxylates having a pKa in the range of about 4-6. These drugs will generally be relatively small, ranging from about 150 to 350 Daltons, having from about 25-65 weight percent of heteroatoms, particularly polar atoms such as oxygen and nitrogen. Other heteroatoms may include halogen, particularly fluoride. The compounds may be cyclic or acyclic, usually cyclic, more usually heterocyclic. Generally, the drugs will have from about 3 to 10, more usually from about 3-8 heteroatoms. These compounds will provide for a significant population, at least about 10%, preferably at least about 30%, more preferably at least about 70%, which are charged at physiological pH, namely a pH of about 7, while having a similar population which is neutral at a pH of about 5. It is particularly preferred to have at least 99% charged molecules at a pH of 7.4. Of particular interest are pyrimidinylcarboxylates, more particularly halogenated pyrimidinylcarboxylates, and 5-fluoroorotate is exemplary.

The liposome composition will be a combination of phospholipids, particularly high-phase-transition-temperature phospholipids, in combination with steriods, particularly cholesterol. Other phospholipids or other lipids may also be employed. Individual or combinations of phospholipids may be employed.

Illustrative lipids include phosphatidyl compounds, such as phosphatidylglycerol, phosphatidylcholine, phosphatidylserine, phosphatidylethanolamine, sphingolipids, cerebrosides, and gangliosides. Of particular interest are diacylphosphatidylglycerols, where the lipids contain from 14-18 carbon atoms, particularly from 16-18 carbon atoms, preferably being saturated.

Exemplary phospholipids include egg phosphatidylglycerol, dipalmitoylphosphatidylglycerol, distearoylphosphatidylglycerol; particulary of interest is dipalmitoylphosphatidylglycerol. Desirably, the phospholipids and steroids will be in a ratio of about 55–75:45–25, usually 60–75:40–25, more particularly 65–70:35–30 molar ratio. Other components of the vesicle bilayer will usually be less than 10 mol %, more usually less than 5 mol %, preferably less than 1 mol %.

In preparing the liposome-encapsulated drug agent, aqueous media will be employed containing various buffers, e.g., phosphate, carbonate, acetate, etc., to provide a pH of from about 6 to 9, more usually from about 6 to 8, preferably from about 6.5 to 7.5. The osmolarity of the medium will be chosen for the ultimate use of the encapsulated drug, particularly being isotonic with a physiological fluid, such as blood, lymph fluid, cerebral spinal fluid, or the like. Generally, the osmolality will be in the range of about 250 to 350, more usually about 275 to 300 mOsm/kg.

Ampholytic compounds employed for preparation of the vesicle of particular interest include morpholinoalkylsulfonates, with alkyl from about 2–4 carbon atoms. Counter ions will be physiologically acceptable counter ions, such as chloride, lithium and sodium.

The drug will have an aqueous solubility of at least 10 mM in the form in which it is employed for encapsulation.

The vesicles are prepared by dispersing or dissolving the drug in an aqueous medium having the appropriate ampholytes and lipids at the appropriate molar ratio. The drug concentration will generally vary from about 0.1 mM to 200 mM, more usually from about 10 mM to about 75 mM. The total concentration of ampholytes will generally range from about 25 to 200 mM, more usually from about 50 to 150 mM. The phospholipid concentration will generally be in the range of 1 to 200 mM, more usually in the range of 5 to 50 mM, with the steroid concentration controlled by the ratio of steroid to phospholipid. As already indicated, other lipids may also be employed which will be substituted for the phospholipid or steroid, according to their nature.

Various techniques may be employed for producing the liposome-encapsulated drug. Of particular interest is a method described by Szoka and Papahadjopoulos (1978) Proc. Nat'l. Acad. Sci. U.S.A., 75:4194–4198, which describes the technique called reverse-phase evaporation. Optionally extrusion is employed to control size (Szoka, et al., biochem, et Biophys. Acta (1980) 601:559–571). Smaller liposomes may be made by sonication of liquid suspensions. The liposomes will be mono- or polylamellar and will be of a size in the range of 0.02 to 100 $\mu$m diameter, usually 0.05 to 1 $\mu$m diameter, preferably 0.1 to 0.7 $\mu$m diameter. Unencapsulated drug may be conveniently removed be gel filtration. The liposomes are then ready to be used or may be modified prior to formulation.

The vesicle bilayers may be modified in a variety of ways. Non-lipid material may be conjugated through a linking group to one or more hydrophobic groups, e.g., alkyl chains from about 12–20 carbon atoms, either prior or subsequent to vesicle formation. The lipid groups are incorporated into the lipid bilayer, so as to maintain such compound in stable association with the bilayer. Various linking groups can be used for joining the lipid chains to the compound. Functionalities of particular interest include thioethers, disulfides, carboxamides, alkylamines, ethers, and the like, used individually or in combination. The particular manner of linking the compound to a lipid group is not a critical part of this invention, the literature providing a great variety of methods. Alternatively, some compounds will have hydrophobic regions or domains, which will allow for their incorporation into the bilayer, without linking to one or more lipid groups.

The number of molecules (either ligand or receptor) bound to a liposome will vary with the size of the liposome, as well as the size of the molecule, the binding affinity of the molecule to the target cell receptor or ligand, and the like. Usually, the bound molecules will be present on the liposome in from about 0.05 to 2 mol %, more usually from about 0.1 to 1 mol %, based on the percent of bound molecules to the total number of molecules in the outer membrane bilayer of the liposome.

For the most part, the compounds to be bound to the lipid bilayer will be ligands and receptors. A ligand may be any compound of interest which will specifically bind to another compound, referred to as a receptor, the ligand and receptor forming an homologous pair. The compounds bound to the bilayer may vary widely, from small haptens of from about 125 to 2,000 molecular weight or higher, to antigens which will generally be at least about 6,000 molecular weight and generally less than about 1 million molecular weight, more usually less than about 300,000 molecular weight. Of particular interest are the proteinaceous ligands and receptors.

A wide variety of compounds which have specific receptors on cell surfaces will be of interest. Illustrative compounds or fragments thereof may include chorionic gonadotropin, enkephalin, $\beta$-endorphin, luteinizing hormone, epidermal growth factor, transforming growth factor, platelet derived growth factor, interleukin-2, morphine, epinephrine, interferon, ACTH, polyiodothyronines, etc.

For the most part, the surface membrane proteins which bind to specific effector molecules are referred to as receptors. However, in the present context, for the most part receptors will be antibodies or immunoglobulins. The immunoglobulins may be monoclonal or polyclonal, preferably monoclonal. Usually, the immunoglobulins will be IgG and IgM, although the other immunoglobulins may also find use, such as IgA, IgD and IgE. The intact immunoglobulins may be used or only fragments thereof, such as Fab, $F(ab')_2$, $F_d$, $F_v$, the light chain and the heavy chain.

For antibodies, antibodies of interest are those that bind to surface membrane antigens such as those antigens comprising the major histocompatibility complex, particularly HLA-A, -B, -C and -D. Other surface antigens include thy-1, leu-5, Ia, etc.

The compositions of this invention provide enhanced drug activity. The compositions may be used in vitro or in vivo. When 5-fluoroorotate is employed, the subject compositions can be employed as cytotoxic agents, inhibiting proliferation and providing for anticontractile activity. These compositions may therefore be used to inhibit the proliferation of particular cells in a mixture of cells, or in tissue, where there is preferential binding and endocytosis of the liposome into the taget cell.

For in vivo application, the liposome-encapsulated drug may be administered in a variety of ways to a host, particularly a mammalian host, such as intravenously, intramuscularly, subcutaneously, intraperitoneally, intravascularly, topically, or the like. Concentration of the drug will vary upon the particular application, the nature of the disease, the frequency of administration, or the like. When employing 5-fluoroorotate, usually the amount of drug employed will be from about 0.05 to 2 mg per administration, more usually from about 0.1 to 0.3 mg. The liposome-encapsulated drug may be provided in a formulation comprising other drugs as appropriate and an aqueous physiologically acceptable medium, e.g., saline, phosphate buffered saline, or the like.

An exemplary of the subject invention is the use of the liposome-encapsulated 5-fluoroorotate for the prevention of scar tissue by inhibiting tissue contraction. Scar tissue formation may result in impaired tissue and organ function, as well as disfiguration.

In particular, the treatment compositions of the present invention are useful for inhibiting scar tissue formation in the eye, referred to as proliferative vitreoretinopathy (PVR), which often results in retinal detachment. Such PVR can result from traumatic injury of the eye, as well as from surgery, such as glaucoma surgery, strabismus surgery, retinal detachment surgery, and the like. Treatment is effected by topical application of the treatment composition to the eye or by intraocular injection. Treatment will usually be repeated daily or more frequently. It has been found that the compositions of the invention including 5-fluoroorotate are highly effective and non-toxic even at elevated concentrations.

The following experiments are offered by way of illustration, not by way of limitation.

EXPERIMENTAL

Materials and Methods

Sodium 5-fluoroorotate (Pharmacia, Piscataway, N.J.) displays a maximum aqueous solubility of 15 mM, while the lithium salt is soluble to at least 50 mM. For encapsulation, a 50 mM lithium 5-fluoroorotate, pH 7.4, 290 mOsm/kg solution was prepared, containing 50 mM morpholinoethanesulfonate and 50 mM morpholinopropanesulfonate, with chloride and lithium counterions. For gel chromatography and subsequent dilution of the liposomes, an equivalent buffer lacking drug was prepared. All solutions were sterilized by filtration prior to use.

All phospholipids (Avanti, Birmingham, Ala.) were used without further purification. Cholesterol (Sigma, St. Louis, Mo.) was recrystallized four times with methanol. All lipids were stored under argon in chloroform solution in sealed ampoules until use. Liposomes were prepared by reverse-phase evaporation (Szoka and Papahadjopoulos (1978) Proc. Natl. Acad. Sci. U.S.A. 75:4194-4198), and extrusion (Szoka et al. (1980) Biochem. et Biophys. Acta. 601:559-571). Small liposomes were made by extensive sonication of lipid suspensions. The unencapsulated drug was removed by gel filtration with Sephadex® G75 (Pharmacia). Lipid concentration was measured by phosporous analysis as described by Bartlett (1959) J. Biol. chem. 234:466-468. The encapsulated drug was measured using a molar extinction coefficient of 7100 in 0.1N HCl. A liposome sample was extracted (Bligh et al. (1959) Can. J. Biochem. Physiol. 37:9911-917), the upper phase was acidified with HCl, and its absorbance was meausred. L929 murine fibroblasts and CV1-P cells were obtained and grown as previously described by Heath et al. (1983) Proc. Natl. Acad. Sci. U.S.A. 80:1377-1381 and Fraley et al. (1980) J. Biol. Chem. 255:10431-10435, respectively. The $IC_{50}$ of the liposome preparations was measured by growth inhibition as previously described by Heath et al. (1983) supra. The cells were incubated for 48 hours (L929) or 72 hours (CV1-P) before counting.

Results

The captured aqueous volumes (Szoka et al. (1980) supra.) are within the expected range for the liposome preparations. This suggests that the drug is encapsulated within the aqueous phase and does not leak rapidly from the liposomes. The liposomes were stored for several weeks at 4° C. without any change in their potency, which further confirms the stability of the preparations.

Unencapsulated 5-fluoroorotate has an $IC_{50}$ of 7 micromolar for CV1-P cells and 1 micromolar for L929 cells (Table 1). When encapsulated in egg phosphatidylglycerol:cholesterol (67:33) liposomes, the potency of 5-fluoroorotate was increased by 2-3 fold. Drug potency was increased 14-35 fold by encapsulation in dipalmitoylphosphatidylglycerol:cholesterol (67:33) liposomes. Sonicated liposomes of this composition were 10 fold less effective than larger liposomes for drug delivery. Drug in distearoylphosphatidylglycerol:cholesterol (67:33) unextruded liposomes was 2-14 times more potent growth inhibitor than free drug. Sonicated liposomes of this composition are less effective than unextruded large liposomes, but the difference is not as great as is seen between sonicated liposomes and unextruded liposomes that contain dipalmitoylphosphatidylglycerol.

TABLE 1

Growth Inhibition by 5-fluoroorotate.

| Lipid[b] | Liposome Properties | | | $IC_{50}{}^a$ (micromolar) | |
| --- | --- | --- | --- | --- | --- |
| | Molar Ratio | Size[c] (μm) | Captured[d] (mol$^{-1}$) | CV1-P | L929 |
| Free Drug[e] | — | — | — | 7 ± 2 | 1.1 ± 0.3 |
| PG:Chol | 67:33 | U | 9.0 | 2.0 | 0.6 |
| | | 0.1 | 2.8 | 2.2 | 0.6 |
| DSPG:Chol | 67:33 | U | 2.8 | 0.5 | 0.72 |
| | | SUV | 0.8 | 0.7 | 0.96 |
| DPPG:Chol | 67:33 | U | 5.2 | 0.2 | 0.08 |
| | | 0.1 | 3.2 | 0.2 | 0.13 |
| | | SUV | 1.2 | 1.7 | 0.8 |

[a]The $IC_{50}$ is the concentration of the drug that inhibits cell growth by 50%.
[b]The lipids used were Chol: cholesterol, PG: egg phosphatidylglycerol, DPPG: dipalmitoylphosphatidylglycerol, DSPG: distearoylphosphatidylglycerol.
[c]The liposomes were prepared by reverse phase evaporation and were either unextruded (U) (0.1 to 1 mM, mean = 0.5 mM) or extruded to 0.1 micrometer (0.1). Liposomes were also prepared by extensive sonication (SUV) (0.03 to 0.07 mM).
[d]The theoretical aqueous capture is the drug:lipid ratio (mol/mol) × the inverse of the orginal drug concentration (0.05 M).
[e]The $IC_{50}$ of the free drug is the mean of 3 determinations for CV1-P cells and of 4 determinations for L929 cells. All other values are derived from individual growth inhibition curves.

As evidenced from the above results, drugs which may otherwise be relatively ineffective because of inability to penetrate the plasma membrane can be encapsulated in liposomes having predetermined size and composition and applied, directly or indirectly, to target cells. The drug is thus found to have greatly enhanced activity as compared to the unencapsulated drug. Furthermore, encapsulation which provides for preferential binding of the liposome to target tissue diminishes adverse effects to normal tissue, while concentrating the drug at the desired site. The subject compositions are easily prepared, are stable for long periods of time, and serve to reduce the drug load to the host by concentrating the drug at a desired site.

Although the foregoing invention has been described in some detail by way of illustration and example for purposes of clarity of understanding, it will be obvious that certain changes and modifications may be practiced within the scope of the appended claims.

What is claimed is:

1. A composition comprising a liposome-encapsulated antiproliferative drug, said drug being a low molecular weight polar carboxylate organic compound having a pKa in the range of about 4 to 6, and said liposome comprising phosphatidylglycerol and cholesterol in a mole ratio of about 55–75:45–25.

2. A composition according to claim 1, wherein said phosphatidylglycerol is a diacylphosphatidylglycerol, wherein the acyl groups contain from 16 to 18 carbon atoms.

3. A composition according to claim 2, wherein said drug is 5-fluoroorotate.

4. A composition according to claim 1, wherein said drug is 5-fluoroorotate.

5. A composition according to claim 4, wherein said phosphatidylglycerol is dipalmitoylphosphatidylglycerol and is in a mole ratio of cholesterol of 60–70:40–30.

6. A composition according to claim 1, wherein said liposome is of a size in the range of about 0.05 to 1.0 μm in diameter.

7. A method for inhibiting cell proliferation employing an antiproliferative drug, said method comprising:
contacting said cell with a proliferation inhibiting amount of a lipid-vesicle-encapsulated drug composition comprising a low molecular weight polar carboxylate antiproliferative drug having a pKa in the range of about 4 to 6 and said liposome comprising at least one phosphatidylglycerol lipid and cholesterol in a ratio of about 55–75:45–25.

8. A method according to claim 7, wherein said contacting is in vitro.

9. A method according to claim 8, wherein said drug is 5-fluoroorotate.

10. A method according to claim 7, wherein said contacting is in vivo.

11. A method according to claim 10, wherein said composition is contacted with the eye to inhibit proliferative vitreoretinopathy.

12. A method according to claim 11, wherein said liposome comprises diacylphosphatidylglycerol, wherein the acyl groups contain from 16 to 18 carbon atoms, and the ratio of phosphatidylglycerol to cholesterol is 60–70:40–30.

13. A method according to claim 12, wherein said acyl group is palmitoyl.

14. A method according to claim 10, wherein said liposome is of a size in the range of about 0.05 to 1.0 μm in diameter.

15. A method according to claim 14, wherein said liposome comprises diacylphosphatidylglycerol, wherein the acyl groups contain from 16 to 18 carbon atoms, and cholesterol in a mole ratio of about 60–70:40–30.

16. A method for inhibiting the formation of scar tissue to traumatized tissue, which comprises:
administering to the traumatized site in an amount sufficient to inhibit cell proliferation a vesicle composition comprising a vesicle consisting essentially of diacylphosphatidylglycerol and cholesterol, wherein said acyl groups contain from 16 to 18 carbon atoms, in a mole ratio of about 60–70:40–30 and a drug in the lumen of said vesicle, said drug being a polar carboxylate of a molecular weight in the range of about 150–350 Daltons and having a pKa in the range of about 4 to 6.

17. A method according to claim 16, wherein said drug is 5-fluoroorotate and said acyl group is palmitoyl.

* * * * *